United States Patent [19]
Colotta et al.

[11] Patent Number: 5,981,713
[45] Date of Patent: Nov. 9, 1999

[54] ANTIBODIES TO INTERELEUKIN-1 ANTAGONISTS

[75] Inventors: Francesco Colotta; Marta Muzio; Alberto Mantovani, all of Milan, Italy

[73] Assignee: Applied Research Systems ARS Holding N.V., Curacao, Netherlands Antilles

[21] Appl. No.: 08/910,884

[22] Filed: Aug. 13, 1997

Related U.S. Application Data

[63] Continuation-in-part of application No. 08/476,860, Jun. 7, 1995, Pat. No. 5,739,282.

[30] Foreign Application Priority Data

Oct. 13, 1994 [IT] Italy .................................. MI94A2097

[51] Int. Cl.$^6$ .................................................. C07K 16/18
[52] U.S. Cl. ..................... 530/387.9; 530/387.1; 530/388.1; 530/388.23; 530/389.1; 530/389.2
[58] Field of Search .............................. 530/387.1, 387.9, 530/388.1, 388.23, 389.1, 389.2, 350

[56] References Cited

U.S. PATENT DOCUMENTS 5,075,222  12/1991  Hannum et al. ........................ 435/69.1

FOREIGN PATENT DOCUMENTS

| A-7363336/91 | 3/1991 | Australia . |
|---|---|---|
| 0 343 684 A1 | 11/1989 | European Pat. Off. . |
| 0 541 920 A1 | 5/1993 | European Pat. Off. . |
| WO 91/08285 | 6/1991 | WIPO . |
| WO 91/17184 | 11/1991 | WIPO . |
| WO 91/17249 | 11/1991 | WIPO . |

OTHER PUBLICATIONS

McColl et al. J. Exp. Med –vol. 176, pp. 593–598, Aug. 1992.

Hannum, Charles H. et al., "Interleukin–1 receptor antagonist activity of a human interleukin–1 inhibitor." Nature, vol. 343, pp. 336–340 (Jan. 25, 1990).

Eisenberg, Stephen P. et al., "Primary structure and functional expression from complementary DNA of a human interleukin–1 receptor antagonist." Nature, vol. 343, pp. 341–346 (Jan. 25, 1990).

Carter, D.B. et al., "Purification, cloning, expression and biological characterization of an interleukin–1 receptor antagonist protein." Nature, vol. 344, pp. 633–638 (Apr. 12, 1990).

Bienkowski, Michael J. et al., "Purification and characterization of interleukin–1 receptor level antagonist proteins from THP–1 cells." Journal of Biological Chemistry, vol. 265, No. 24, pp. 14505–14511(1990).

Stockman et al. Secondary Strucutre and Topology of Interleukin–1 Receptor Antagonist Protein Determined by Heteronuclear Three–Dimensional NMR Spectroscopy, American Chemical Society vol. 31, No. 23, pp. 5237–5244, Jun. 19, 1992.

Interleukin 1 Receptor Antagonist is a Member of the Interleukin 1 Gene Family: Evolution of a Cytokine Control Mechanism, Proc. Natl. Acad. Sci., vol. 88, pp. 5232–5236, Jun. 1991.

Haskill et al, cDNA Cloning of an Intracelluar Form of the Human Interleukin 1 Receptor Antagonist Associated with Epithelium, Proc. Natl. Acad. Sci., vol. 88 pp. 3681–3685, May 1991.

C. Butcher et al. "Comparison of two promoters controlling expression of secreted or intracellular IL–1 receptor antagonist", Journal of Immunology, vol. 153, Jul. 1994, pp. 701–711.

C. A. Dinarello et al. "Blocking IL–1: Interleukin 1 receptor antagonist in vivo and in vitro", Immunology Today, vol. 12, No. 11, 1991, Cambridge GB, pp. 404–410.

N.F. Zander et al. "cDNA cloning and complete primary structure of skeletal muscle phosphorylase kinase (alpha subunit)", Proceedings of the National Academy of Sciences USA, vol. 85, May 1988, Washington US, pp. 2929–2933.

Abstract, EMBL database entry SKADECYC Accession No. X56042 (version 1); Nov. 19, 1990; Young et al.

M. Muzio et al. "Cloning and charcterization of a new isoform of the interleukin 1 receptor antagonist", Journal of Experimental Medicine, vol. 182, No. 2, Aug. 1, 1995, pp. 623–628.

Primary Examiner—Prema Mertz
Attorney, Agent, or Firm—Browdy and Neimark

[57] ABSTRACT

A novel interleukin-1 antagonist active against both IL-1α and IL-1β and DNA encoding same/re described. Antibodies specific for the novel IL-1 antagonist and prophylatic, therapeutic and diagnostic uses of the IL-1 antagonist in pathologies associated with IL-1 production are also described.

2 Claims, 6 Drawing Sheets

FIG. 1

Secreted IL-1ra

GAATTCCGGGCTGCAGTCACAGAGAATGGAAATCTGAGAGGCCTCACCTAATCACTCCTCCTCCTCTTCCATTCAG
　　　　　　　　　　　　　　　　　MetGluIleCysArgGlyLeuArgSerHisLeuIleThrLeuLeuPheHisSer

Intracellular IL-1ra type I

← IRA 1

CAGAAGACCTCCTGTCCTATGAGGCCCTCCCCATGGCTTTAG
　　　　　　　　　　　　　　　　　MetAlaLeu

Intracellular IL-1ra Type II

← IRA 1　　　　　　　　　　　　　　　　　　　　　IRA 5 →

CAGAAGACCTCCTGTCCTATGAGGCCCTCCCCATGGCTTTAGCTGACTTGTATGAAGAAGGAGGTGGAGGAGGAAGGTGAAGACAATGCTGACTCAAAGG
　　　　　　　　　　　　　　　　　MetAlaLeuAlaAspLeuTyrGluGluGlyGlyGlyGlyGlyGlyGluGlyGluAspAsnAlaAspSerLys

Common IL-1ra sequence

AGACGATCTGCCACCCTCTGGGAGAAATCCAGCAAGATGCAAGCCTTCAGAATCTGGATGTTAACCAGAAGACCTTCTATCTGAGGAACAACCAACTAGTT
GluThrIleCysArgProSerGlyArgLysSerLysMetGlnAlaPheArgIleTrpAspValAsnGlnLysThrPheTyrLeuArgAsnAsnGlnLeuVal

GCTGGATACTTGCAAGGACCAAATGTCAATTTAGAAGAAAGATAGAGTGGTACCATTGAGCCTCATGCTCTGTCTTCTTGGAATCCATGGAGGGAAGATGTGC
AlaGlyTyrLeuGlnGlyProAsnValAsnLeuGluGluLysIleAspValValProIleGluProHisAlaLeuPheLeuGlyIleHisGlyGlyLysMetCys

CTGTCCTGTGTCAAGTCTCGGTGATGAGACCAGATCCGAGCCAGTTAACATCACTGACCTGAGCGAGAACAGAAGCAGGACAAGCGCTTCGCCTTCATC
LeuSerCysValLysSerGlyAspGluThrArgLeuGlnLeuGluAlaValAlaAsnIleThrAspLeuSerGluAsnArgLysGlnAspLysArgPheAlaPheIle

CGCTCAGACAGTGGCCCCACCACCAGTTTGAGTCTGCCGCCCGTTGTTCCTCTGCACAGCGATGAAGCTGACCAGCCCGTCAGCCTCAGCTCACCAATATG
ArgSerAspSerGlyProThrThrSerPheGluSerAlaAlaCysProGlyTrpPheLeuCysThrAlaMetGluAlaAspGlnProValSerLeuThrAsnMet

CCTGACGAAGGCGTCATGGTCACCAAATTCTACTTCCAGGAGGAGTAGTAC
ProAspGluGlyValMetValThrLysPheTyrPheGlnGluAspGlu*

← IRA 4

ANTIBODIES TO INTERELEUKIN-1 ANTAGONISTS

CROSS-REFERENCE TO RELATED APPLICATIONS

The present application is a continuation-in-part of U.S. application Ser. No. 08/476,860, filed Jun. 7 1995 now U.S. Pat. No. 5,739,282, the entire contents of which are hereby incorpated by reference.

FIELD OF THE INVENTION

The present invention is in the field of biotechnology, and relates to a novel interleukin-1 (IL-1) antagonist active against both IL-lα and IL-Iβ, to antibodies specific to this novel IL-1 antagonist, to a new DNA sequence encoding the IL-1 antagonist and to a method for obtaining a IL-1 antagonist by recombinant DNA techniques. The present invention also relates to the prophylactic, therapeutic and diagnostic use of such a novel IL-1 antagonist in pathologies associated with the IL-1 production.

BACKGROUND OF THE INVENTION

Two distinct genes, designated IL-1α and IL-1β, encode for interleukin-1 (IL-1) proteins IL-lα and IL-1β, respectively.

Interleukin IL-1α and IL-1β are pleiotropic cytokines, and each, despite little sequence homology between them, exerts a variety of similar effects on different tissues and act on many human pathologies, and particularly on the immune response of the organism and on inflammatory processes. Both proteins have a molecular weight of about 17.5 kDa and are synthesized as a larger precursor molecule having a molecular weight of about 31 kDa.

IL-1 proteins are potent inflammatory and pyrogenic cytokines that normally have beneficial effects, but that can also have extremely harmful effects on the organism. For example, IL-1 proteins participate in the pathogenesis of autoimmune pathologies, such as lupus erythematosus, and in particular, they are involved as mediators that provoke damage to tissues, as for example in rheumatoid arthritis.

Many of the biological effects of IL-1 are similar to those observed during sepsis. Recent studies demonstrated that the intravenous administration of IL-1 in a dosage range from 1 to 10 ng/kg gives rise to fever, sleepiness, anorexy, generalized myalgia, arthralgia and cephalea. Since IL-1 has pleiotropic biological activities, many of which negatively influence the organism, the powerful effects of IL-1 should be put under strict physiological control.

The synthesis of IL-proteins is inhibited by anti-inflammatory cytokines, prostaglandins and glucocorticoids and the existence of multiple levels of inhibition of IL-1 points to the necessity for strict control of this mediator. To date, IL-1 is the only cytokine for which an antagonist polypeptide for the receptor has been described; the third known component of the IL-1 family is the antagonist for the IL-1 receptor (IL-1ra).

All three components (IL-lα, IL-1β, IL-1ra) recognize and bind to the same receptor on the cell surface (IL-1R); the binding of IL-1α and IL-1β to IL-1R transmit a signal, whereas the binding of IL-1ra does not. There are two types of IL-1 receptors designated IL-1RI and IL-1RII. IL-1ra is a polypeptide which binds to IL-1RI, and also binds to IL-1RII with less affinity, without any agonistic activity.

IL-lra production is induced in different types of cells, including mononuclear phagocytes, polymorphonuclear cells (PMN) and fibroblasts, by IgG, cytokines and bacterial products. Until now, only two molecular forms of IL-lra have been identified and cloned:

1) secreted IL-lra (sIL-1ra) contains a classical leader sequence of 25 amino acids giving a mature protein of 152 amino acids;
2) intracellular IL-lra (icIL-1ra) lacks a leader sequence and it is predicted that this protein remains intracellular. sIL-1ra and icIL-1ra are generated from the same gene.

The human genes coding for IL-1α and IL-1β and IL-1ra belongs to the same gene family and are clusterized on chromosome 2 mapping to the q12-q21 region (Eisenberg et al., Proc. Natl. Acad. Sci. USA 88:5232, 1991). The human IL-1ra gene has been partially sequenced and characterized. As shown in FIG. 5, the human IL-1ra gene contains in its 3' region, three exons coding for the C-terminal common part of the three isoforms of IL-1ra (exons 2, 3 and 4 in FIG. 5) and in its 5' region, three exons which can be differentially spliced to generate the three isoforms of the antagonist (exons ic1, ic2 and s1 in FIG. 5). The 3' part of the gene between the promoter of the secreted isoform and the last exon of the gene, as well the region upstream the first intracellular specific exon, have been sequenced (bold line in FIG. 5) (Butcher et al., J. Immunol.153:701, 1994; Lennard et al., Cytokine 4:83, 1992). On the other hand, the part of the gene between the promoter region of sIL-ra and first exon of icIL-1ra was unknown (thin line in FIG. 5).

Transcripts of icIL-1ra1 originate from an alternative starting site and from the splicing of a first alternative exon into an internal splice acceptor site located in the first exon of sIL-lra. The predicted proteins are thus identical except in their $NH_2$ ends, where the first 21 amino acids of sIL-1ra are substituted by four amino acids in icIL-Ira. The expression of transcripts encoding sIL-lra and icIL-lra is regulated differently, and the biological significance of icIL-lra is still unclear.

Considering that IL-1 is involved in pathogenesis of many diseases, it is evident that there is a need for medicaments which are useful in limiting the harmful effects of IL-1.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

An object of the present invention is to provide an IL-1 antagonist active against both IL-lα and IL-1β and against a combination thereof.

Another object of the present invention is to provide a DNA sequence encoding an IL-1 antagonist and a method for obtaining such a novel antagonist by recombinant DNA techniques.

A further object of the present invention is to provide an antagonist in substantially purified form so as to be suitable for use in pharmaceutical compositions active in pathologies that can be treated by inhibiting IL-1.

Yet another object of the invention is to provide antibodies specific for the IL-1 antagonist.

Further objects and advantages of the invention will be evident in the following description.

BRIEF DESCRIPTION OF THE DRAWINGS

FIG. 1 shows the DNA sequence and the amino acid sequence, for the portion which is not in common, of the icIL-1raII protein (SEQ ID NO:7 and SEQ ID NO:8) compared to those of classic sIL-1ra (icIL-1raI; SEQ ID NO:6) and of sIL-1ra (SEQ ID NO:4 and SEQ ID NO:5), and it further shows the DNA sequence and the encoded protein sequence for the portion of IL-1ra in common (SEQ ID NO:12 and SEQ ID NO:13). Arrows indicate forward (IRA 1 and IRA 5) and backward (IRA 4) oligonucleotides used for RT-PCR analysis, as described in the text. The oligonucleotide IRA 5 recognizes only icIL-1reII DNA. The asterisk indicates the stop codon.

DETAILED DESCRIPTION OF THE INVENTION

Figure 2A:
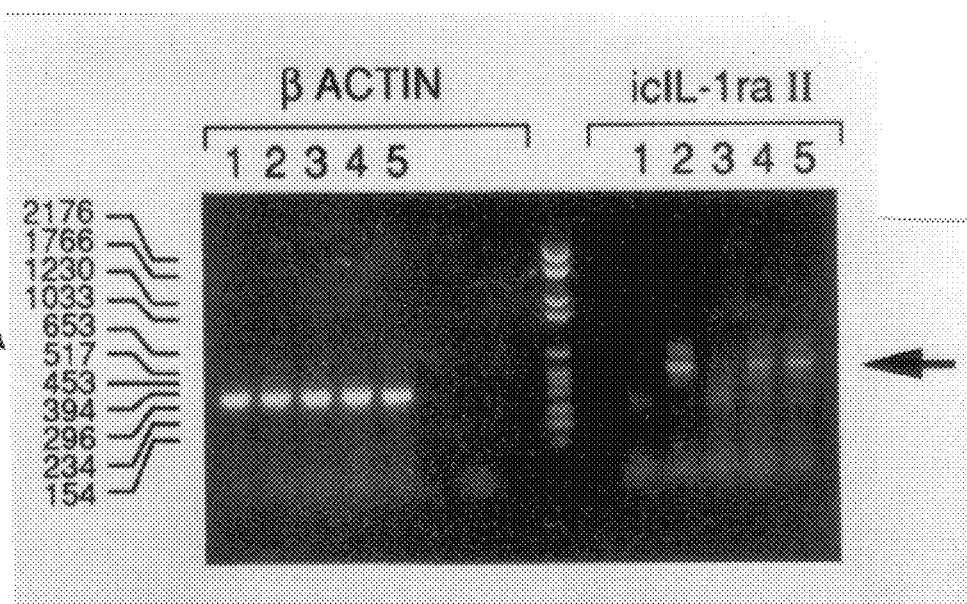
FIGS. 2A–2C show the RT-PCR analysis of icIL-1raII expression in different cell types. RNAs from 8387 fibroblasts (FIG. 2A), monocytes (FIG. 2B) and PMN (FIG. 2C) were reverse-transcribed. Each DNA synthesis reaction was then divided into two samples, one of which was amplified with oligonucleotides IRA 5 (forward) and IRA 4 (backward) for detection of icIL-1raII transcripts, and the other sample was amplified with β-actin specific oligonucleotides (see Material and Methods section). Amplified products were then examined through an ethidium bromide-stained agarose gel. Amplified products corresponding to β-actin are reported on the left side of the standard and the amplified products corresponding to icIL-1raII (on the right) are indicated by an arrow. The specificity of these bands was confirmed by subcloning and sequencing.

The novel IL-1 antagonist was generated by inserting a new 63 base pairs (bp) sequence between the first icIL-1ra specific exon and the internal acceptor site of the first exon of sIL-1ra and in frame with the DNA encoding icIL-1ra.

The present inventors found using RT-PCR that this novel transcript is expressed in activated monocytes and fibroblasts and in polymorphonuclear cells (PMN). Expression in COS cells revealed that this novel antagonist is mostly intracellular and has a molecular weight (MW) of approximately 25 kDa in SDS-PAGE.

The novel recombinant antagonist was demonstrated to have IL-1 inhibitory activity.

The known icIL-1ra will be referred to as icIL-1ra type I (icIL-1raI), and the novel antagonist, described here and the object of the present invention, will be referred to as icIL-1ra type II (icIL-1raII).

Examples of pathologies in which the novel antagonist according to the present invention can be advantageously used for prophylactic, therapeutic or diagnostic purposes are rheumatoid arthritis, septic shock, acute myelomonocytic leukemia, immunological reaction of transplant against host, acquired immunodeficiency syndrome (AIDS), ulcerative colitis and all autoimmune diseases in general.

An embodiment of the invention is the administration of a pharmacologically active amount of icIL-1raII to people having a high risk of developing pathologies that can be treated by inhibiting IL-1 or to people already showing pathologies like sepsis. An example of the category cited above are patients waiting for a surgical operation.

Any route of administration compatible with the active principle can be used, but parenteral administration is particularly preferred because it permits systemic effects in a short period of time. For this reason, it is preferable that the administration of an intravenous bolus is given just before, during or after the surgical operation. The dose of icIL-1raII to be administered depends on the age, weight and the individual response of the patient. The dosage can be between 0.05 and 30 mg/Kg body weight and the preferable dose is between 0.1 and 10 mg/Kg body weight.

The pharmaceutical composition for parenteral use can be prepared in injectable form and comprises an active principle and a suitable vehicle. Vehicles for the parenteral administration are well known in the art and comprise, for example, water, saline solution, Ringer's solution and dextrose. The vehicle can contain smaller amounts of excipients in order to maintain stability in solution and isotonicity.

The preparation of the above-cited solutions can be carried out according to the ordinary modalities and preferably the icIL-1raII content will be between 1 mg/ml and 10 mg/ml.

Further examples of pathologies wherein the novel antagonist according to the invention can be advantageously used for prophylactic, therapeutic, or diagnostic purposes are rheumatoid arthritis, septic shock, acute myelomonocytic leukemia, immunological reaction of transplants against host, acquired immunodeficiency syndrome (AIDS), ulcerative colitis and all autoimmune diseases in general.

It should be understood that when the term "antibodies" is used with respect to the antibody embodiments of the present invention, this is intended to include intact antibodies, such as monoclonal or polyclonal antibodies, as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al., Br. J. Cancer Suppl., 10:27–9 (1990); Gross, G. et al., Proc. Natl. Acad. Sci. USA, 86:10024–8 (1989)). Single chain antibodies can also be produced and used. Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$–$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091, 513 and 5,096,815, the entire contents of each of which are hereby incorporated herein by reference.

A molecule which includes the antigen-binding portion of an antibody, is intended to include not only intact immunoglobulin molecules of any isotype and generated by any animal cell line or microorganism, but also the reactive fraction thereof including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction.

The antibodies and molecules which include the antigen-binding portion of an antibody specific for icIL-1raII according to the present invention can be used to purify icIL-1raII, such as by affinity chromatography. The availability of icIL-lraII specific antibodies also provides an invaluable tool in pathophysiology, where preliminary experiments in the laboratory of the present inventors suggest that icIL-1raII is indeed expressed under inflammatory conditions in humans.

Having now generally described the invention, the same will be more readily understood through reference to the following example which is provided by way of illustration and is not intended to be limiting of the present invention. In the section that follows, some methods for obtaining the invention will be described, although equivalent materials and methods can be used. The following examples are therefore purely illustrative and are non-limiting examples of the invention.

EXAMPLE 1

Cloning and Characterization of icIL-lraII

MATERIALS AND METHODS

Reagents

The following commercially available reagents were used for the culture and separation of cells: pyrogen-free saline and distilled water for clinical use; RPMI 1640 medium; DMEM medium; M199 medium; L-glutamine; Percoll; Ficoll-Hypaque; aseptically collected fetal calf serum; endothelial cell growth supplement (ECGS) prepared from bovine brain; Heparin. All reagents contained less than 0.125 EU/ml of endotoxin as confirmed by the Limulus amebocyte lysate assay.

Cells

Human circulating PMN and monocytes were separated from the peripheral blood of healthy donors by centrifugation on a discontinuous (46% for monocytes and 62% for PMN) gradient of isosmotic (285 mOsm) Percoll as described in Colotta F., Peri G., Villa SA., Mantovani A., Rapid killing of actinomycin D treated tumor cells by human mononuclear cells. *J. Immunol.* 132:936, 1984. Cells were recovered at the interface, washed twice in saline, and resuspended in medium.

PMN and monocytes recovery was higher than 90% and the purity was higher than 98% as assessed by morphological examination of stained cytocentrifuged cells. The cell culture medium routinely used for PMN and monocytes was RPMI 1640 with 2 mM L-glutamine and 10% FCS.

Human endothelial cells (EC) were obtained from umbilical veins and cultured as described in detail in the literature (Allavena P., Paganin C., Martin-Padura I., Peri G., Gaboli M., Dejana E., Marchisio P. C., Mantovani A., Molecules and structures involved in the adhesion of natural killer cells to vascular endothelium, *J. Exp. Med.*, 173:439, 1991).

Confluent cells at 2nd-5th passage maintained in Ml99 medium with 10% FCS supplemented with ECGS (50 µg/ml) and Heparin (100 µg/ml were routinely used.

COS cells were cultivated in DMEM medium with 10% FCS and 8387 fibroblast cells in RPMI 1640 medium with 10% FCS.

After the appropriate treatment, the cells were examined for IL-1ra mRNA or IL-1ra protein as described below.

RT-PCR

Total RNA was extracted by the guanadium isothiocyanate method with minor modifications.

RT-PCR was performed as described in Colotta F., Polentarutti, N., Sironi M., Mantovani A., *J.Biol.Chem.*, 267:18278, 1992.

Briefly, 1 µg RNA was reverse transcribed in reverse transcriptase buffer (5 mM MgCl$_2$, 50 mM KCl, 10 mM Tris-HCl; pH 8.3) with 2.5 mM random hexamers, 1 mM each deoxynucleotide triphosphate, 1 unit/ml RNase inhibitor, and 2.5 units/ml moloney murine leukemia virus transcriptase (Perkin Elmer Cetus, Norwalk, Conn.). Samples were incubated for 10 min at 25° C. and then at 42° C. for 45 min. Then, a specific pair of primers, designed to amplify cDNAs encoding icIL-1raI or icILlraII, were added to the cDNA reaction, and, as an internal control, human β-actin was added.

Amplification was carried out in 2 mM MgCl$_2$, 50 mM KCl, 0.2 M of each deoxynucleotide triphosphate, 2.5 units/ 100 ml Taq polymerase (Perkin Elmer Cetus) and 4 mg/ml of each specific primer (see below). Amplification (30 cycles) was carried out in an automated thermal cycler (Perkin Elmer Cetus) at 95° C., at 55° C., and at 72° C. for 1.5 min each. Amplified products were run through a 1% ethidium bromide-stained agarose gel along with molecular weight standards (Boehringer Mannheim, Mannheim, Germany).

Oligonucleotides were synthesized by the phosphoramidite method. The sequences of oligonucleotides used to selectively amplify icIL-lra were identical to those described in Haskill S. et al., *Proc. Natl. Acad. Sci., USA*, 88:3681, 1991. In particular, oligonucleotides GM397 (indicated here as IRA 1) and GM368 (IRA 4) was used. For the icIL-1raII amplification, IRA 4 and IRA 5 (SEQ ID NO:1), which specifically recognizes the extra exon described here to be included in the icIL-1raII sequence, were used.

For β-actin amplification the forward oligonucleotide is presented in SEQ ID NO:2, corresponding to nucleotides 60–79 of β-cDNA. The backward oligonucleotide presented in SEQ ID NO:3, is complementary to nucleotides 430–449. The amplification products were subcloned (TA Cloning System, Invitrogen, San Diego, Calif.) and sequenced by the dideoxy chain termination method.

Analysis of Genomic DNA

Genomic DNA was extracted from human circulating monocytes following standard protocols. 0.5 mg of genomic DNA was amplified at 94° C. for 1 min., 60° C. for 1 min. and 70° C. for 4 min. Oligonucleotide primers used were IRAL (see above), IRA9 (SEQ ID NO:14), IRA 7 (SEQ ID NO:15) and IRA10, which is identical to B(BS1.1). Amplification products were subcloned (TA Cloning System, Invitrogen, San Diego, Calif.) and sequenced by the chain termination method. Analysis of the sequence was performed with the Proexplore software package (Oxford Molecular Ltd., Oxford, UK).

Generation of Anti-icIL-1raII Antiserum

The peptide of SEQ ID NO:16 was conjugated to BSA by coupling with glutaraldehyde. 15 mg of protein were injected three times into rabbits s.c. at two week intervals. The antiserum was tritiated by ELISA on peptide-coated plates.

Expression of icIL-1ra Products in COS Cells

The cDNAs containing 32 bp of the 5'-untranslated region, the complete open reading frame and 6 bp (including the stop codon) of the 3'-untranslated region of both the icIL-lral and icIL-lraII were obtained by RT-PCR with oligonucleotides IRA 4 and IRA 5 as described above and then ligated back into the pSF5 expression vector. Fidelity of reverse transcription and amplification was verified by sequencing.

The plasmids containing the cDNA in the correct orientation were purified on CsCl gradient and then transfected into COS cells by the calcium precipitate method as described in Sambrook J. et al., Cold Spring Harbor Laboratory Press, 1989.

After two days, culture supernatants and sonicated cell lysates were examined by ELISA or immunoblotting as described below. An empty plasmid (not transfected) was used as a control.

Identification of Immunoreactive IL-lra

A commercial ELISA test (Amersham, Buckinamshire, UK) that identifies both sIL-lra and 1cIL-ira was used. For the Western blot analysis, polyclonal antisera of two rabbits and of one goat were used. COS cell lysate samples and supernatants were run on 12.5% SDS-PAGE electrophoresis and then blotted onto a nitrocellulose filter (Stratagene, La Jolla, Calif., USA). Incubation with primary and secondary antibodies was carried out according to standard protocols. The primary antibody was an anti-IL-1ra rabbit polyclonal antibody. The secondary antibody was a goat anti-rabbit immunoglobulin fraction linked to horseradish peroxidase (Amersham). Immunoreactive protein fraction bands were revealed by a chemiluminescence-based procedure (ECL Detection, Amersham) according to manufacturer's instructions.

Il-1-induced Expression of E-selectin on EC

Confluent EC cultivated in 96 well plates (Falcon) were incubated for 30 minutes with an amount of transfected COS cell lysate (see above) corresponding to 25 to 100 ng of recombinant IL-1ra (either icIL-1raI or icIL-1raII) as assessed by a specific ELISA assay (Amersham).

As a control, an equal amount of COS lysate obtained from mock transfected cells was used in parallel. Next, EC were exposed for 6 hours to 0.1–1 ng/ml human recombinant IL-1β. The detection of E-selectin expression was made with an ELISA assay on adherent EC with the anti-E-selectin monoclonal antibody BB1G-E2 as primary antibody and a rabbit anti-mouse Ig antiserum conjugated with horseradish peroxidase as a secondary antibody. Optical Density (O.D.) of the samples was determined by measuring the plates with a spectrophotometer (Flow) at 405 nm wavelength.

RESULTS

Identification of icIL-1raII

Specific oligonucleotide primers were designed (indicated as IRA 1 and IRA 4 in FIG. 1) in order to obtain the entire coding sequence of icIL-1ra (FIG. 1) by RT-PCR. Amplified products from human PMN were subcloned and sequenced.

In addition to the previously known sequence of icIL-1ra, the present inventors isolated a number of clones whose sequences were identical to the published icIL-1ra coding sequence, with the notable exception of an extra sequence of 63 bp between nucleotides 132 and 133 of the icIL-1ra sequence. Given the described exon-intron boundaries of icIL-1ra, the extra sequence is inserted between the first leader-less exon of icIL-1ra and the internal acceptor site of the first exon of sIL-1ra (FIG. 1).

The predicted amino acid sequence is shown in FIG. 1. The novel protein (herein referred to as icIL-1ra type II) has the first three amino acids at the $NH_2$ terminus in common with the classical icIL-1ra (icIL-1ra type I), followed by a new sequence of 21 amino acids. The rest of the two proteins is identical.

The entire sequence for each molecule is thus generated by the junction of each specific portion with the common sequence. For clarity, the DNA sequence of icIL-1ra starts from nucleotide 91 of the published 5' untranslated sequence, and only 6 bp of the 3' untranslated sequence are reported. The common IL-1ra sequence (SEQ ID NO:9) starts with the internal acceptor site located in the first exon of sIL-1ra, corresponding to nucleotide 133 of the complete icIL-1raI sequence and to nucleotide 88 of the complete sIL-lra sequence.

With regard to questions related to the "Patentin" program for the preparation of the sequences, a G nucleotide was added in the first position of the sequence in order to encode for the first amino acid Glu, and further in order to avoid the formation of a stop codon in the inner side of the sequence.

SEQ ID NO:10 reports the amino acid sequence of IL-1ra for the portion which is in common and SEQ ID NO:11 reports the sequence of 21 amino acids representing an icIL-1raII fragment not in common with the other IL-1ras.

Surprisingly, the junction with the internal acceptor site of the first exon of sIL-1ra, both for sIL-1ra and icIL-1raI and for icIL-1raII, always generated the same amino acid residue, i.e. glutamic acid (FIG. 1).

The most striking characteristic of the extra inserted amino acid sequence is the presence of seven glycine residues, six of which are consecutive. Glycine residues are flanked on both sides by glutamic acid residues. icIL-1raII consists of 180 amino acids, and the overall hydrophilic pattern of icIL-1raII is similar to that of icIL-lraI, and still lacks an hydrophobic leader peptide at the $NH_2$ terminus.

Expression of icIL-raII

Figure 2B:
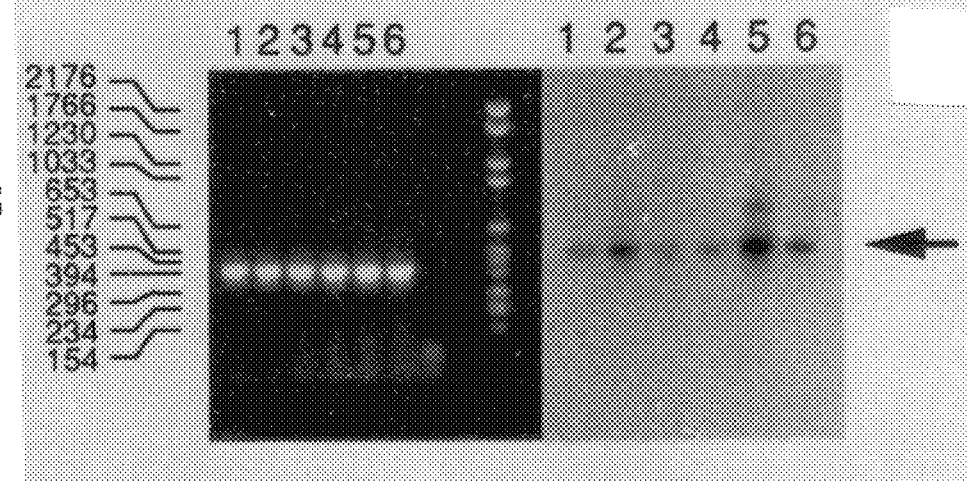
Figure 2C:
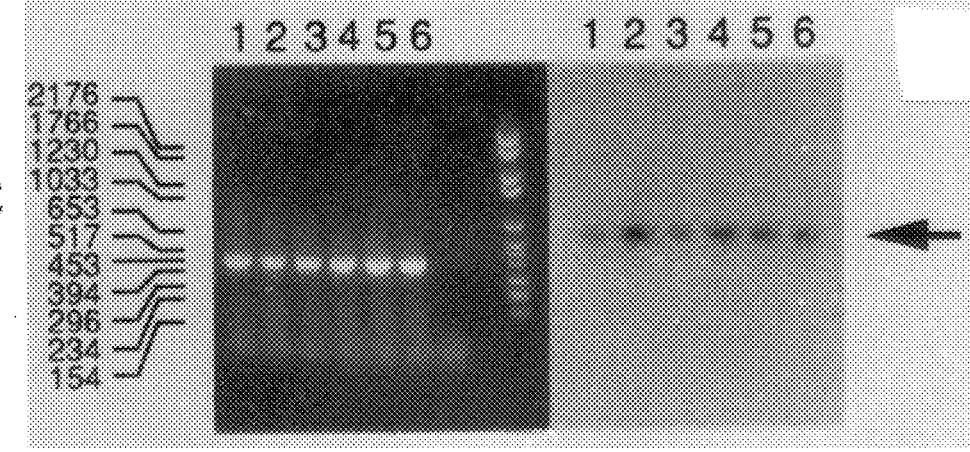

To identify icIL-1raII transcripts, RT-PCR analysis was performed with a pair of specifically designed oligonucleotides (IRA 5 and IRA 4, FIG. 1), with an expected amplified product of 533 bp. As shown in FIG. 2A, transcripts encoding icIL-1raII were detectable in PMA-, IL-1- and TNF-activated fibroblasts. A faint but detectable band was evident in LPS-treated monocytes. PMN, either untreated or activated (FIG. 2C), also showed a very faint band of the expected size. The specificity of amplified products indicated in FIGS. 2A–2C was confirmed by subcloning and sequencing.

Expression of Recombinant icIL-lraII

COS cells were transfected with the DNA sequence encoding icIL-1raII and, by way of comparison, with that encoding icIL-1raI. Next, cell lysates and supernatants were examined by Western blot.

Figure 3:
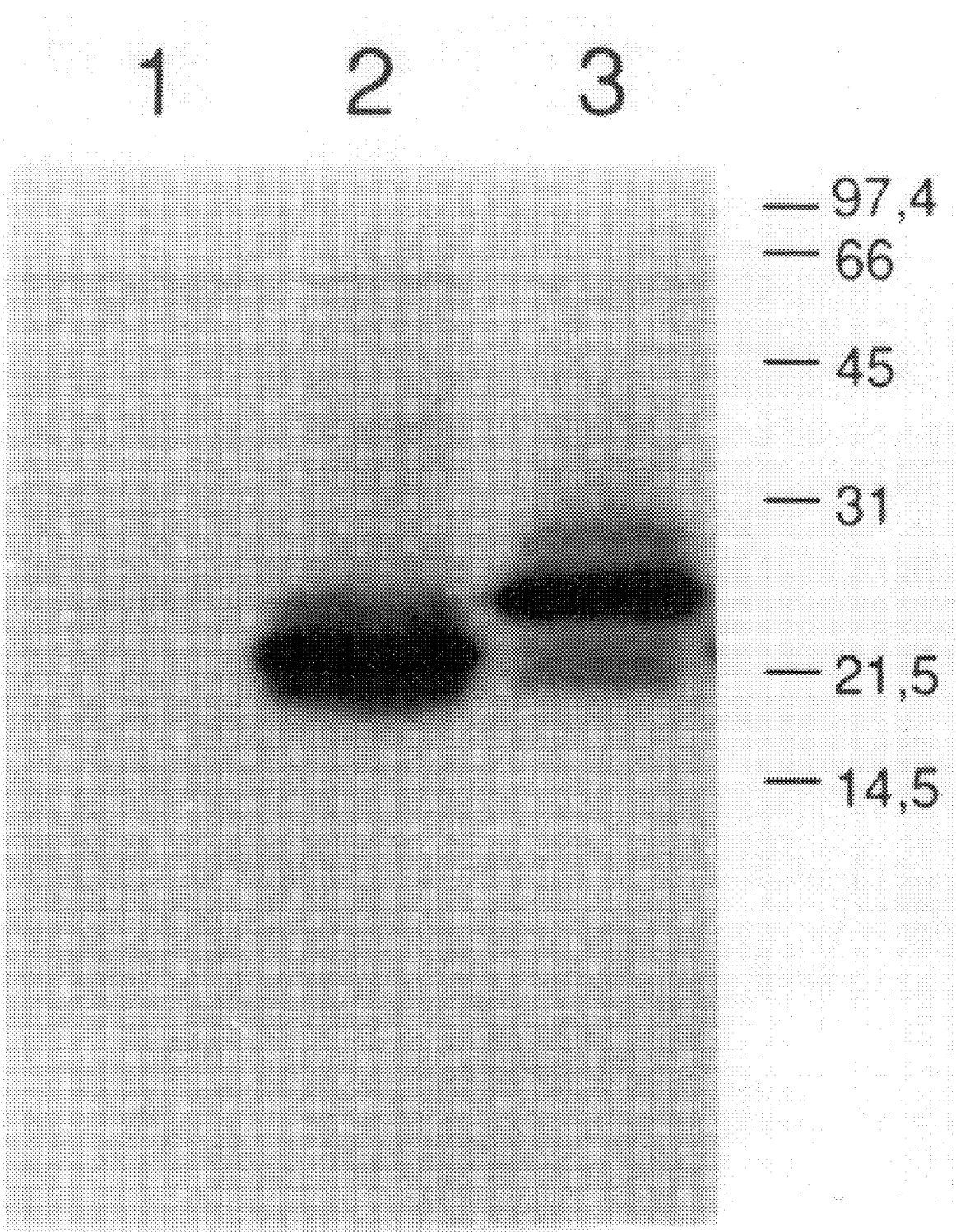
FIG. 3 shows the Western blot analysis of recombinant icIL-1raII. Cell lysates from COS cells transfected with DNAs encoding icIL-1raI (lane 2) or icIL-1raII (lane 3) or with an empty vector which does not contain such DNA (lane 1) were examined by immunoblotting with an anti-IL-1ra rabbit polyclonal antibody. Molecular weight standards are indicated on the right.

The polyclonal antisera used in these experiments recognized icIL-1raII and icIL-1raI equally well (FIG. 3). Most, if not all, of icIL-1raII and icIL-1raI were found in cell lysates. Recombinant icIL-1raI migrated as a predominant band of 22 kDa, whereas icIL-iraII showed a mass of approximately 25 kDa.

Figure 6:
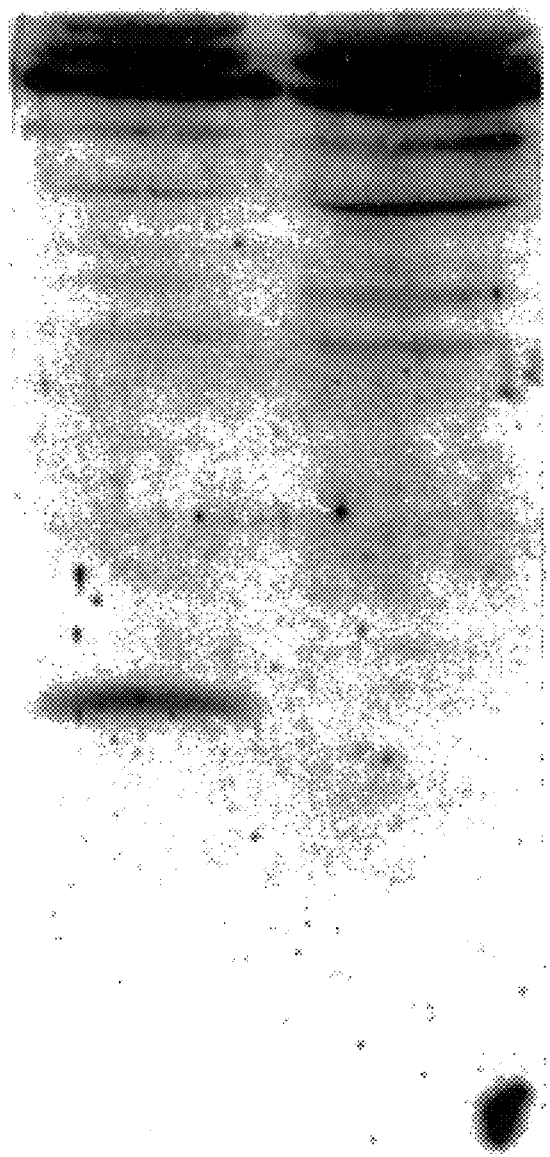
FIG. 6 shows the detection of icIL-1raII by Western blot with rabbit serum. 100 μg of COS cells are transformed with icIL-1raII lysate (lane 1) or icIL-1raI (lane 2).

The recognition of icIL-1raII by anti-icIL-1raII antiserum was checked by Western blotting icIL-1raII expressed in COS cells (FIG. 6). As a comparison, soluble IL-1ra was used with negative results.

Inhibition of IL-1B Activity by Recombinant icIL-1raII

Recombinant icIL-1raII was examined for IL-1 inhibiting activity using IL-1-induced expression of E-selectin on endothelial cells. This assay is sensitive (detectable induction at 100 pg/ml IL-1, or less) and rapid (6 hours incubation with IL-1).

Figure 4A:
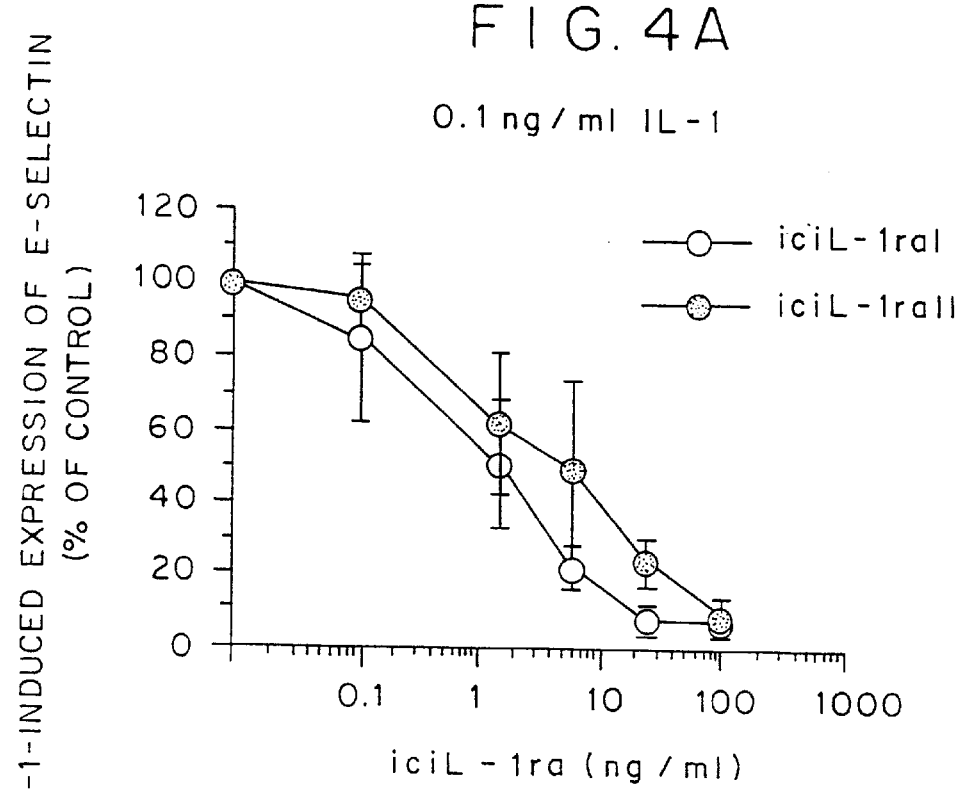
FIGS. 4A–4B show the effects of icIL-1raII on IL-1 induced expression of E-selectin in endothelial cells. Endothelial cells were treated with 0.1 (FIG. 4A) or 1 ng/ml (FIG. 4B) of human IL-1β, with or without 25–100 ng/ml of icIL-1raII or equivalent amounts of COS cell lysates obtained from cells which were mock transfected by means of an empty vector, as described in the Material and Method section. After 6 hours of incubation, the endothelial cells were examined for E-selectin expression by an ELISA test performed on adherent cells. The data reported are percentages of IL-1-induced E-selectin expression for the control.
Figure 4B:
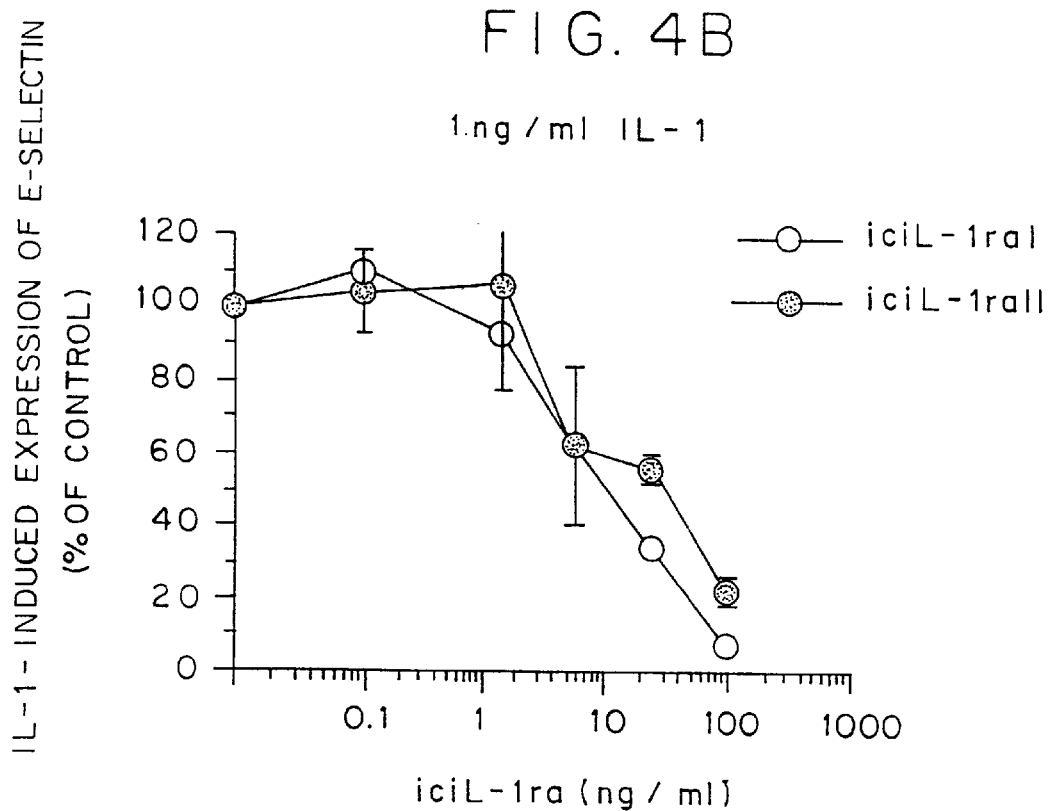

Lysates of mock transfected COS cells did not significantly reduce IL-1 activity. icIL-1raII had no antagonistic activity. As shown in FIGS. 4A–4B. recombinant icIL-1raII inhibited in a dose-dependent fashion IL-1 activity. These data provide evidence that icIL-1raII is indeed an inhibitor of IL-1.

Characterization of Human IL-1ra Genomic DNA

PCR amplification of human genomic DNA was performed in order to clone a portion of the human IL-1ra gene containing the exon specific for icIL-1raII. The icIL-1ra first exon had been previously localized approximately 9.4 kb upstream of the sIL-1ra first exon (Butcher et al., J. Immunol. 153:701 (1994)), but sequence information was available only for a region of 6.2 kb located immediately upstream of the sIL-1ra first exon (Butcher et al., J. Immunol. 153:701 (1994); Lennard et al., Cytokine 4:83 (1992)). This intronic sequence did not contain the extra exon specific for icIL-1raII. The laboratory of the present inventors previously demonstrated that the extra exon specific for icIL-1raII is localized in the remaining 3.2 kb genomic sequence not yet available (Muzio et al., J. Exp. Med., 182:623 (1995)). An IRA 10 oligonucleotide, which is colinear with the most 5' sequence of the known intronic sequence (Butcher et al., J. Immunol. 153:701 (1994), was designed and IRA 1 oligonucleotide, whose sequence is contained within the icIL-1ra first exon, were used in the PCR amplification.

Figure 5:
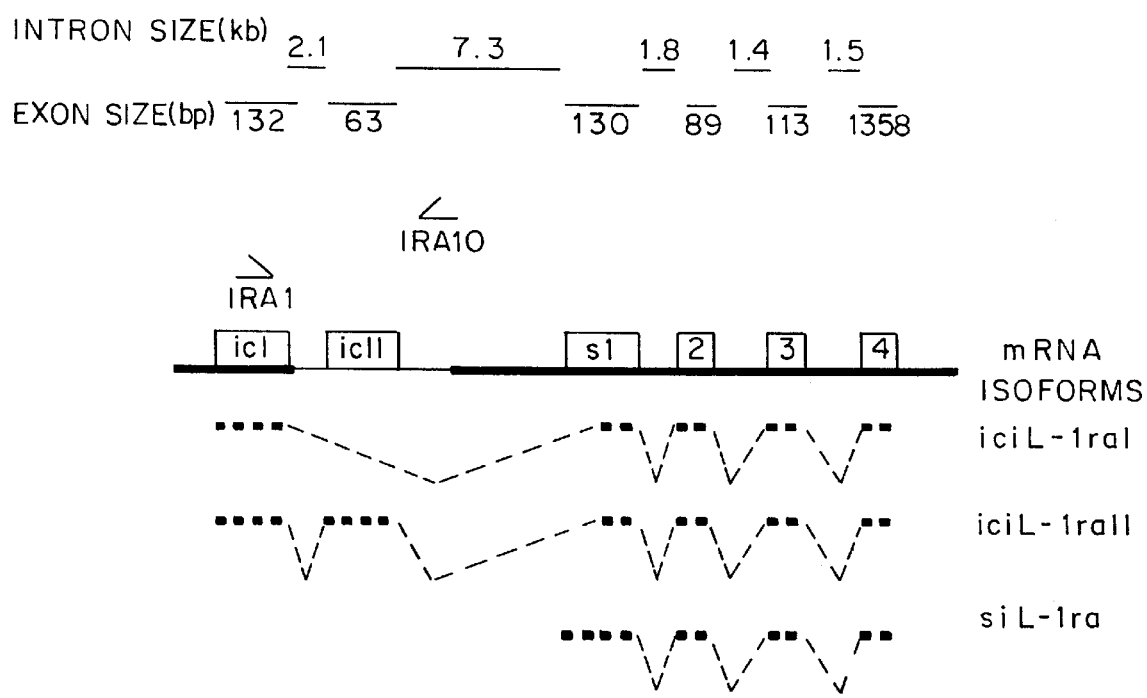
FIG. 5 shows the organization of the human IL-1ra gene. The boxes represent the exons (the size is not representative of the actual length in bp), where icI indicates the first exon of the intracellular form, icII indicates the new exon, s1 refers to the first exon of the soluble form, and 2, 3, and 4 indicate the 3' exons. The characterized isoforms described are schematically represented below the human IL-1ra gene and the lengths of the exons and introns are indicated above. The PCR primers that were used are indicated with arrows. The known sequence of the gene is indicated with a bold line and the previously unknown sequence of the gene is indicated with a thin line.

A genomic fragment of 3.2 kb was amplified, cloned and sequenced (SEQ ID NO:17). The corresponding sequence of 63 nucleotides was found at a distance of 2037 bases downstream relative to the icIL-1raI first exon and was flanked by the exon-intron junction consensus AG and GT nucleotides (Mount, Nucl. Acid. Res. 10:45 (1982)). The region immediately upstream relative to the new exon does not contain an ATG codon, thus suggesting that probably it is not a first exon, but rather an internal extra exon which can be spliced under precise stimuli (FIG. 5). Similarly to the known sequence of the IL-1ra gene, this region of the gene contains an Alu-type sequence between bases 760 and 1000.

An 86 bp sequence, tandem repeated, was present in the intron located downstream with respect to the first sIL-1ra specific exon (Lennard et al., Cytokine 4:83 (1992)), where polymorphism in the number of repeats has been previously shown (Tarlow et al., Human Genet 91:403–404 (1993)) and a specific allele has been associated with production of different cytokines (Danis et al., Clin Exp. Immunol. 99:303–310 (1995)) and specific diseases (Clay et al., Hum. Genet. 94:407–10 (1994)). Interestingly, the 86 bp repetition contains three potential binding sites, an α-interferon silencer A, a β-interferon silencer B and an acute phase response element. In the first intron, downstream with respect to the icIL-iraI specific exon, a 13 bp sequence in position 1114 which is repeated in position 1142 was found where this sequence contains a LBP-1 consensus motif (FIG. 5 in the boxes).

DISCUSSION

The present inventors describe a novel molecular form of icIL-1ra which is generated by insertion of 63 bp between the first leader-less exon of icIL-1ra and the internal acceptor site of the first exon of sIL-lra. Since the resulting protein is partially identical to classical icIL-1ra, with the exception of an extra sequence of 21 amino acids located in the $NH_2$ terminus of the molecule, the present inventors suggest that this novel form be designated as IL-1ra type II, and referring to the classical icIL-lra sequence as icIL-1ra type I.

RT-PCR experiments demonstrated that icIL-1raII transcripts are inducible in monocytes and fibroblasts. Recombinant icIL-1raII expressed in COS cells had an apparent MW of approximately 25 kDa and an IL-1 inhibitory activity comparable to that exerted by icIL-1raI expressed under the same experimental conditions. Transcripts coding for icIL-1ra and sIL-1ra were generated from the same gene by means of differential splicing. icIL-1ra was generated from an alternative start of transcription of an exon inserted into an internal acceptor site of the first exon containing the leader sequence of sIL-1ra.

The results obtained by the present inventors suggest a new organization for the IL-1ra gene, in which an extra exon is located between the first exon of, respectively, classical icIL-1ra and sIL-1ra. The presence of this extra exon generates a polypeptide molecule which lacks a signal peptide, but differs from icIL-1raI at its N-terminus by the insertion of 21 amino acids, and still remains inhibitory against IL-1.

The use of alternative splicing to generate different IL-1ra molecules appears to be highly regulated. icIL-1raII transcripts were induced by IL-1, TNF and phorbol esters in fibroblasts and by LPS in monocytes. In fibroblasts, phorbol esters were found to selectively induce icIL-1ra transcripts, whereas IL-1 and TNF induced both sIL-1ra and icIL-1ra mRNAs. In monocytes, IL-13, which augmented both transcripts of sIL-1ra and icIL-1raI, failed to induce icIL-1raII.

Finally, PMN, in which sIL-1ra and icIL-1ra are constitutively expressed and inducible, expressed very few transcripts, as demonstrated by RT-PCR. Overall, these results indicate that the mechanisms that induce the differential splicing, which generate the three forms of IL-1ra, are differentially regulated in response to external signals.

The amino acid sequence of the extra sequence described here is surprising in that it contains seven residues of glycine, six of which are consecutive. Glycine-rich sequences are present in molecules with different biological activities, including the atrial natriuretic clearance receptor, the HOX11 homeobox gene, the intermediate filaments keratins and nuclear proteins involved in centromere binding or RNA splicing.

Apart from glycine residues, however, no obvious homology was evident between these proteins and icIL-1raII in the amino acid sequence flanking the glycine-rich regions.

The IL-1 system shows an extraordinary level of complexity, and consists of two agonists, two receptors, one of which is an inhibitor of IL-1, and a receptor antagonist, for which at least three different molecular forms exist, as shown by the results obtained.

Although the biological significance of the intracellular forms of IL-1ra remains to be clearly established, the results reported here indicate that two different forms of icIL-1ra with different N-termini can be generated by alternative splicing in response to selected external stimuli.

The existence of multiple and complex levels of control of IL-1 points to the absolute requirement for a tight physiological control of the inflammatory potential of this cytokine.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patents applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: RT-PCR oligonucleotide named IRA5

(xi) SEQUENCE DESCRIPTION: SEQ ID NO: 1:

CTGACTTGTA TGAAGAAGGA GGTGG                                       25

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (iii) HYPOTHETICAL: NO (ix) FEATURE:
            (D) OTHER INFORMATION: RT-PCR oligonucleotide corresponding
                to 60-79 of B-actin (xi) SEQUENCE DESCRIPTION: SEQ ID NO: 2:

GCGCTCGTCG TCGACAACGG                                                     20

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (ix) FEATURE:
            (D) OTHER INFORMATION: RT-PCR backward oligonucleotide
                complementary to 430-449

(xi) SEQUENCE DESCRIPTION: SEQ ID NO: 3:

GATAGACAAC GTACATGGCT G                                                   21

(2) INFORMATION FOR SEQ ID NO: 4:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: DNA (iii) HYPOTHETICAL: NO (ix) FEATURE:
            (D) OTHER INFORMATION: Sequence of sIL-1ra not in common (ix) FEATURE:
            (A) NAME/KEY: CDS
            (B) LOCATION: 24..86

(xi) SEQUENCE DESCRIPTION: SEQ ID NO: 4:

GAATTCCGGG CTGCAGTCAC AGA ATG GAA ATC TGC AGA GGC CTC CGC AGT             50
                        Met Glu Ile Cys Arg Gly Leu Arg Ser
                         1               5

CAC CTA ATC ACT CTC CTC CTC TTC CTG TTC CAT TCA G                         87
His Leu Ile Thr Leu Leu Leu Phe Leu Phe His Ser
 10              15                  20

(2) INFORMATION FOR SEQ ID NO: 5:

(i) SEQUENCE CHARACTERISTICS:
            (A) LENGTH: 21 amino acids
            (B) TYPE: amino acid
            (D) TOPOLOGY: linear (ii) MOLECULE TYPE: protein (xi) SEQUENCE DESCRIPTION: SEQ ID NO: 5:

Met Glu Ile Cys Arg Gly Leu Arg Ser His Leu Ile Thr Leu Leu Leu
 1               5                  10                  15

Phe Leu Phe His Ser
              20

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Sequence of intracellular IL-1ra
            typeI not in common (ix) FEATURE:
        (A) NAME/KEY: CDS
        (B) LOCATION: 33..41

(xi) SEQUENCE DESCRIPTION: SEQ ID NO: 6:

```
CAGAAGACCT CCTGTCCTAT GAGGCCCTCC CC ATG GCT TTA G                42
                                     Met Ala Leu
                                      1
```

(2) INFORMATION FOR SEQ ID NO: 7:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Sequence of intracellular IL-1ra
            typeII not in common (ix) FEATURE:
        (A) NAME/KEY: CDS
        (B) LOCATION: 33..104

(xi) SEQUENCE DESCRIPTION: SEQ ID NO: 7:

```
CAGAAGACCT CCTGTCCTAT GAGGCCCTCC CC ATG GCT TTA GCT GAC TTG TAT      53
                                     Met Ala Leu Ala Asp Leu Tyr
                                      1               5

GAA GAA GGA GGT GGA GGA GGA GGA GAA GGT GAA GAC AAT GCT GAC TCA     101
Glu Glu Gly Gly Gly Gly Gly Gly Glu Gly Glu Asp Asn Ala Asp Ser
         10              15                  20

AAG G                                                               105
Lys
```

(2) INFORMATION FOR SEQ ID NO: 8:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Leu Ala Asp Leu Tyr Glu Glu Gly Gly Gly Gly Gly Glu
 1               5                  10                  15

Gly Glu Asp Asn Ala Asp Ser Lys
```

(2) INFORMATION FOR SEQ ID NO: 9:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Common IL-1ra sequence; a nucleotide G
        was added in the first position, for computer program
        reason, in order to encode the first amino acid Glu
        and further in order to avoid the creation of a stop
        codon in the inner region of the sequence (ix) FEATURE:
        (A) NAME/KEY: CDS
        (B) LOCATION: 1..468

(xi) SEQUENCE DESCRIPTION: SEQ ID NO: 9:

```
GAG ACG ATC TGC CGA CCC TCT GGG AGA AAA TCC AGC AAG ATG CAA GCC        48
Glu Thr Ile Cys Arg Pro Ser Gly Arg Lys Ser Ser Lys Met Gln Ala
 1               5                  10                  15

TTC AGA ATC TGG GAT GTT AAC CAG AAG ACC TTC TAT CTG AGG AAC AAC        96
Phe Arg Ile Trp Asp Val Asn Gln Lys Thr Phe Tyr Leu Arg Asn Asn
            20                  25                  30

CAA CTA GTT GCT GGA TAC TTG CAA GGA CCA AAT GTC AAT TTA GAA GAA       144
Gln Leu Val Ala Gly Tyr Leu Gln Gly Pro Asn Val Asn Leu Glu Glu
        35                  40                  45

AAG ATA GAT GTG GTA CCC ATT GAG CCT CAT GCT CTG TTC TTG GGA ATC       192
Lys Ile Asp Val Val Pro Ile Glu Pro His Ala Leu Phe Leu Gly Ile
    50                  55                  60

CAT GGA GGG AAG ATG TGC CTG TCC TGT GTC AAG TCT GGT GAT GAG ACC       240
His Gly Gly Lys Met Cys Leu Ser Cys Val Lys Ser Gly Asp Glu Thr
65                  70                  75                  80

AGA CTC CAG CTG GAG GCA GTT AAC ATC ACT GAC CTG AGC GAG AAC AGA       288
Arg Leu Gln Leu Glu Ala Val Asn Ile Thr Asp Leu Ser Glu Asn Arg
                85                  90                  95

AAG CAG GAC AAG CGC TTC GCC TTC ATC CGC TCA GAC AGT GGC CCC ACC       336
Lys Gln Asp Lys Arg Phe Ala Phe Ile Arg Ser Asp Ser Gly Pro Thr
            100                 105                 110

ACC AGT TTT GAG TCT GCC GCC TGC CCC GGT TGG TTC CTC TGC ACA GCG       384
Thr Ser Phe Glu Ser Ala Ala Cys Pro Gly Trp Phe Leu Cys Thr Ala
        115                 120                 125

ATG GAA GCT GAC CAG CCC GTC AGC CTC ACC AAT ATG CCT GAC GAA GGC       432
Met Glu Ala Asp Gln Pro Val Ser Leu Thr Asn Met Pro Asp Glu Gly
    130                 135                 140

GTC ATG GTC ACC AAA TTC TAC TTC CAG GAG GAC GAG TAGTAC               474
Val Met Val Thr Lys Phe Tyr Phe Gln Glu Asp Glu
145                 150                 155
```

(2) INFORMATION FOR SEQ ID NO: 10:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO: 10:

```
Glu Thr Ile Cys Arg Pro Ser Gly Arg Lys Ser Ser Lys Met Gln Ala
 1               5                  10                  15

Phe Arg Ile Trp Asp Val Asn Gln Lys Thr Phe Tyr Leu Arg Asn Asn
             20                  25                  30

Gln Leu Val Ala Gly Tyr Leu Gln Gly Pro Asn Val Asn Leu Glu Glu
         35                  40                  45

Lys Ile Asp Val Val Pro Ile Glu Pro His Ala Leu Phe Leu Gly Ile
 50                  55                      60

His Gly Lys Met Cys Leu Ser Cys Val Lys Ser Gly Asp Glu Thr
 65              70                  75              80

Arg Leu Gln Leu Glu Ala Val Asn Ile Thr Asp Leu Ser Glu Asn Arg
                 85                  90                  95

Lys Gln Asp Lys Arg Phe Ala Phe Ile Arg Ser Asp Ser Gly Pro Thr
             100                 105                 110

Thr Ser Phe Glu Ser Ala Ala Cys Pro Gly Trp Phe Leu Cys Thr Ala
             115                 120                 125

Met Glu Ala Asp Gln Pro Val Ser Leu Thr Asn Met Pro Asp Glu Gly
 130                 135                 140

Val Met Val Thr Lys Phe Tyr Phe Gln Glu Asp Glu
 145                 150                 155

(2) INFORMATION FOR SEQ ID NO: 11:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (ix) FEATURE:
        (D) OTHER INFORMATION: A portion of the intracellular IL-1ra
            typeII not in common (xi) SEQUENCE DESCRIPTION: SEQ ID NO: 11:

Ala Asp Leu Tyr Glu Glu Gly Gly Gly Gly Gly Glu Gly Glu Asp
 1               5                  10                  15

Asn Ala Asp Ser Lys
             20

(2) INFORMATION FOR SEQ ID NO: 12:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (D) OTHER INFORMATION: Intracellular IL-1ra typeII (ix) FEATURE:
        (A) NAME/KEY: CDS
        (B) LOCATION: 34..573

(xi) SEQUENCE DESCRIPTION: SEQ ID NO: 12:

CAGAAGGACC TCCTGTCCTA TGAGGCCCTC CCC ATG GCT TTA GCT GAC TTG TAT         54
```

```
                        Met Ala Leu Ala Asp Leu Tyr
                          1               5
GAA GAA GGA GGT GGA GGA GGA GAA GGT GAA GAC AAT GCT GAC TCA         102
Glu Glu Gly Gly Gly Gly Gly Glu Gly Glu Asp Asn Ala Asp Ser
             10                  15                  20

AAG GAG ACG ATC TGC CGA CCC TCT GGG AGA AAA TCC AGC AAG ATG CAA     150
Lys Glu Thr Ile Cys Arg Pro Ser Gly Arg Lys Ser Ser Lys Met Gln
         25                  30                  35

GCC TTC AGA ATC TGG GAT GTT AAC CAG AAG ACC TTC TAT CTG AGG AAC     198
Ala Phe Arg Ile Trp Asp Val Asn Gln Lys Thr Phe Tyr Leu Arg Asn
 40                  45                  50                  55

AAC CAA CTA GTT GCT GGA TAC TTG CAA GGA CCA AAT GTC AAT TTA GAA     246
Asn Gln Leu Val Ala Gly Tyr Leu Gln Gly Pro Asn Val Asn Leu Glu
                 60                  65                  70

GAA AAG ATA GAT GTG GTA CCC ATT GAG CCT CAT GCT CTG TTC TTG GGA     294
Glu Lys Ile Asp Val Val Pro Ile Glu Pro His Ala Leu Phe Leu Gly
             75                  80                  85

ATC CAT GGA GGG AAG ATG TGC CTG TCC TGT GTC AAG TCT GGT GAT GAG     342
Ile His Gly Gly Lys Met Cys Leu Ser Cys Val Lys Ser Gly Asp Glu
         90                  95                 100

ACC AGA CTC CAG CTG GAG GCA GTT AAC ATC ACT GAC CTG AGC GAG AAC     390
Thr Arg Leu Gln Leu Glu Ala Val Asn Ile Thr Asp Leu Ser Glu Asn
105                 110                 115

AGA AAG CAG GAC AAG CGC TTC GCC TTC ATC CGC TCA GAC AGT GGC CCC     438
Arg Lys Gln Asp Lys Arg Phe Ala Phe Ile Arg Ser Asp Ser Gly Pro
120                 125                 130                 135

ACC ACC AGT TTT GAG TCT GCC GCC TGC CCC GGT TGG TTC CTC TGC ACA     486
Thr Thr Ser Phe Glu Ser Ala Ala Cys Pro Gly Trp Phe Leu Cys Thr
                140                 145                 150

GCG ATG GAA GCT GAC CAG CCC GTC AGC CTC ACC AAT ATG CCT GAC GAA     534
Ala Met Glu Ala Asp Gln Pro Val Ser Leu Thr Asn Met Pro Asp Glu
            155                 160                 165

GGC GTC ATG GTC ACC AAA TTC TAC TTC CAG GAG GAC GAG TAGTAC          579
Gly Val Met Val Thr Lys Phe Tyr Phe Gln Glu Asp Glu
        170                 175                 180

(2) INFORMATION FOR SEQ ID NO: 13:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 13:

Met Ala Leu Ala Asp Leu Tyr Glu Glu Gly Gly Gly Gly Gly Glu
 1               5                  10                  15

Gly Glu Asp Asn Ala Asp Ser Lys Glu Thr Ile Cys Arg Pro Ser Gly
                 20                  25                  30

Arg Lys Ser Ser Lys Met Gln Ala Phe Arg Ile Trp Asp Val Asn Gln
         35                  40                  45

Lys Thr Phe Tyr Leu Arg Asn Asn Gln Leu Val Ala Gly Tyr Leu Gln
     50                  55                  60

Gly Pro Asn Val Asn Leu Glu Glu Lys Ile Asp Val Val Pro Ile Glu
 65                  70                  75                  80

Pro His Ala Leu Phe Leu Gly Ile His Gly Gly Lys Met Cys Leu Ser
                 85                  90                  95

Cys Val Lys Ser Gly Asp Glu Thr Arg Leu Gln Leu Glu Ala Val Asn
            100                 105                 110
```

```
Ile Thr Asp Leu Ser Glu Asn Arg Lys Gln Asp Lys Arg Phe Ala Phe
            115                 120                 125

Ile Arg Ser Asp Ser Gly Pro Thr Thr Ser Phe Glu Ser Ala Ala Cys
130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TTTGAGTCAG CATTGTCTTC A                        21

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTGACTTGTA TGAAGAAGGA GGTGG                  25

(2) INFORMATION FOR SEQ ID NO:16:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ala Asp Leu Tyr Glu Glu Gly Gly Gly Gly Gly Glu Gly Glu Asp
1               5                   10                  15

Asn Ala Asp Ser Lys
            20
```

(2) INFORMATION FOR SEQ ID NO:17:

(i) SEQUENCE CHARACTERISTICS:
        (A) LENGTH: 3176 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CAGAAGACCT CCTGTCCTAT GAGGCCCTCC CCATGGCTTT AGGTAAGCTC CTTCCACTCT    60

CATTTTTTCA CCTGAGAAAT GAGAGAGGAA AATGTCTACA ATTGGTGTTT ATCAAATGCT   120

```
TTCAGGCTCT GGTGAGCAAG CGTCCAGGAA AATGTCAAGC GCATGGAGCT CCAGGCCTGT      180

CTGGGGGATC TGGGCACGGG GAGGCATCCA TGGGAGACCA TGCAGGCACT CTGAGGCAGG      240

GGCTGCAAGC TAGTGCCTGC TGGGGCAGCA GGTGAACAGA GAGGTGTAAC TGCTGTGACA      300

GAAGTCATGG AGTCCTTGGA GTGTGAGGGT CATTTTCCAC TGTTGATAGA ATAGGGAAAT      360

TGGTGAAATA GCCCTGTTAA ATGAGAGAAA GAACAGTGTG AGCTCAATGA GAAATACTAA      420

TAGAATGTGG CACTGAGCCA CAAGGTCTGA GGGTTGATTG ATAAGGAAGG GTGGGACTG       480

TGGAGAATTA AGGGCTTGGC ACAGGTCAGT TCCACCAGTT GTCACAAGAG AATGCAGGCT      540

CAGGTGGCCA GAACTTCTCG CTTTTCCAGA AGAGTCCGAT ATTCTGATTT CATTATATAT      600

AGTATTCTGA TTAAACCAGA CAATAAAGCA AGCAGATAAA ATATTTAAAG TATAAGCTGC      660

CAGTTTGCAA CCTCCGGTTA GGATTTGTGT GGGCAAAGA AAAAAACTCT CAGGATCATT       720

GGTATGTAGA CTCTAATTTT AAGTTTCTAA TTTAAAATTG GCCCCTGAGG CTGGGCGTGG      780

TGGCTCACAC CTGTAATCCC AGCATTTTGG GAGGCCAAGG TGGGTGGATC TCTTGAGGTC      840

AAGAGTTCAA GGCCTGCCTG GCCAACATGG TGAAACCCTG TCTCTATTAA AAATACAAAA      900

ATTAGCTGGG CATGGTGGTG CATGTCTGCA ATCTTAGCTA CTTGGGTAGC TAAGGCAGGA      960

GAATTGCTGG AACCCGGGAG GTAGAGGTTG CAGTGAATGG AGATCACACC ACTGCACTCC     1020

AGTCTGGGCA ATAGAGAGAG ACGCTCTCTC TAAAAAAAAA TATGTAAAGA TAAATAAAAT     1080

GAAATAAAAT AGGCCTCTAA TGAGCAGGCC ATTCTCCTTT CTGGGTCTTA CTTTCCTTGC     1140

ACTCCTTTCT GGGTGTTAAG AGGAGGTCTA GAGGAAGCTG GACAACTCTT AGCTTGTAGT     1200

AAGCACAGTG GAAGTATCAG CTCTTAATGG GTCATGGACA CGTTACGAAG CTAGGCGCCG     1260

TGCTGAGCAC TTTACATGGT TTATCCCACT GAACCCTCTC AATAACCCTA TGAGGAAGGG     1320

CTATTATTGC TCACATTTTC AGAAGAGGAA ATGGATATAG AGAGATTAGA TAATTTGCCC     1380

ATGGCCAGAC AGCTAGTATA AGAGGAGGAG GTGGATTGAC TGCAGACATT CTGTCTTCAA     1440

ACCACTACAC TATGCTATGG AGGCACAGAG ACTTAATGAA ATCATGGAGA GGGGAATTGC     1500

TTTGTCAACC ACAAGCAGTT ATTCCGGGGG CAGCAGATCC TCCCCTGTCC CCCAGTGGTA     1560

CAATGGTCCC TGGTGGGTTG TGCTACAATG TTAGCCCATG GTCTTATGTG TTTTTCAAAT     1620

GTGTAAAGTA GGATGCTGGA ACCACTCTTA GAACCAGATA CCAATACATT GTGAAGAAAT     1680

AAATCTCTGT GCTTAAAACT GGTTCATCCC AAAATATTTT GAACTGACAC ACAATAGGTG     1740

CTAAATAAAT GTGTGTTAAC TTGAATTGGA TTGAATTCGG GAAAAAAGTG CAATAAGCTT     1800

AGTGAAGACA CCATGTTCCC TGGGTAGAGG AACCACATTC TCCATATAAG GCCAGGAGTA     1860

TGGGAGGTAT CAATGTTTGC CCAGCACAGA ACAGGGTGCC AAGAAGAGAA AAGTTGACGG     1920

GGTGCATACT CTGACTGGAA ACTGGAAGGG TGAGAACAGA GGGTAAAGGA TAGAGATGGA     1980

ACCATGTGCA TACACTTTGT GTTACCTTGG ACAAGTCATT CATTTCTCTG GACCTCTGCT     2040

TTCTCTCTAC ACAATGGGGT CCCACCACTT CCCTTACAGC TGACTTGTAT GAAGAAGGAG     2100

GTGGAGGAGG AGGAGAAGGT GAAGACAATG CTGACTCAAA GGGTAAATTA TTTTTAGGAT     2160

CCAAGTTTGA AAACAATTTT AGGCTACTAG ATATGAACAA CATCTTGATT ATGTAGTTGA     2220

AGGAAATTAA AGATGAATGG TTTAATTAAA AATTAATCAG AATGAAAACG ATTGATTACT     2280

AATATATCTG CAATGGTTTA TTTTCCTGAG TGGCAGACTC ACTAAGGTTT TGAATACTC      2340

CTGTGTGATT GCTCTATGTA TGTATGTATG TATGTATGTA TGCATGTATC TATCTATCTG     2400

TTGTCTAATA GAATGGATCA CATCTCTGCT AATAAAAACA CTACACTGGC AGGGTACAAT     2460

TATAATCATT AACTGTGCCT GGAATTTGCA GCAGCAGCCA CCAGAGGTAC CAGTGCCCTT     2520
```

-continued

```
TAAGGGTTCA TAATTTAGAA TAATCCAATT ATCTGAGTTT TTCAGGGACT GAGGGGTTTG    2580

GCAAGGTGTA GAACTTTCAG TAATAAAGTC AAGAAAGTCC TGGACAAACC AAGGTAGTTG    2640

GTCACTCTAG TCCATAACCA GGTAAAGAGC TTTCCCTGTA ACCTGTGTAA GGTTTTAGAA    2700

TCATTTCTTT CCTTATTACC AAAAATCCTC CCCAAATTTT CAAGAAATTA TGAACTAAAT    2760

AGTTACTCTA TGAGATAGGA GTTCAGCCCA AAAGAAACAC CATAAGAACA AATATAATTC    2820

TTGCTTATGT TAACCATGCA ATGAAGCAGA GAGAAAAAGT CAGTGGCCTC TTTAGGAGGA    2880

CTGTAGTGTG GGAAGAAATA ACTAAACTGG GTTTCAATCC TGGCCTGGCC AGGATCTGGA    2940

GCAAGTGAGT TAATCTTTCA AAGCCTTGAG TAGTTTATAA AAGAATGGCC ACTCCATAGA    3000

CAGAGTAGCC TGAACCTTGA GTTCTTCTAT AAAGTCACTA TGAATTTATA CTCATTTTGA    3060

AAGTGGGTGT CAATATGTCT GTCCACTTTG CACAGCTGTT ATGTGGACAA AAGGAGATCT    3120

GTGTGAAAGT GTAACACAGA GCCTAAACTA TAACAGGTAA GCAACACAGT TGTCCC       3176
```

What is claimed is:

1. An isolated antibody specific for an epitope of an interleukin-1 receptor antagonist, wherein said epitope is located within an amino acid sequence of SEQ ID NO:11 of said interleukin-1 receptor antagonist.

2. The isolated antibody according to claim 1, wherein said isolated antibody is a monoclonal antibody.

* * * * *